United States Patent [19]

Smith, Jr.

[11] Patent Number: 5,303,579

[45] Date of Patent: Apr. 19, 1994

[54] CONVEYOR-BELT MOISTURE CONTROL SENSOR APPARATUS

[75] Inventor: Donald G. Smith, Jr., Tazewell, Va.

[73] Assignee: MEFCOR, Inc., Bluefield, Va.

[21] Appl. No.: 12,643

[22] Filed: Feb. 3, 1993

[51] Int. Cl.$^5$ .................. B65G 49/00; G01N 27/04
[52] U.S. Cl. ........................................ 73/73; 198/495
[58] Field of Search ............................ 73/73; 198/459

[56] References Cited

U.S. PATENT DOCUMENTS

| | | | |
|---|---|---|---|
| 1,708,073 | 4/1929 | Allen | 73/73 X |
| 2,829,340 | 4/1958 | Lippke. | |
| 3,332,279 | 7/1967 | Tompos et al. | 73/73 |
| 3,358,378 | 12/1967 | Downs | 73/73 X |
| 3,713,966 | 1/1973 | Lippke. | |
| 3,731,520 | 5/1973 | Hickman et al. | |
| 4,055,077 | 10/1977 | Loch. | |
| 4,427,976 | 1/1984 | Lord. | |
| 4,944,385 | 7/1990 | Shelby. | |

FOREIGN PATENT DOCUMENTS

| | | | |
|---|---|---|---|
| 146030 | 11/1980 | Japan | 73/73 |
| 153252 | 9/1982 | Japan | 73/73 |

Primary Examiner—Daniel M. Yasich
Attorney, Agent, or Firm—Griffin, Butler, Whisenhunt & Kurtossy

[57] ABSTRACT

A conveyor-belt moisture control sensor apparatus (10) includes a sensor device (12) having an electrically-insulative block (30) with two adjacent electrodes (32, 34) extending therefrom to contact a top surface (22) of a return portion (24) of a conveyor belt (26). Two wires (36, 38) are mounted on the electrically-insulative block and connected to connection ends of the electrodes at encapsulated points in the electrically-insulative block. A hinge mechanism (40) mounts the electrically-insulative block to a conveyor-belt support frame (44) for allowing the electrically-insulative block to rotate, thereby bringing the electrodes into contact with the conveyor belt. A drip guard (98) extends from the electrically-insulative block above the electrodes.

18 Claims, 2 Drawing Sheets

CONVEYOR-BELT MOISTURE CONTROL SENSOR APPARATUS

BACKGROUND OF THE INVENTION

This invention relates generally to the art of endless conveyor belts and more particularly to apparatus for monitoring and maintaining moisture contents of such conveyor belts.

When aggregate material, such as coal, for example, is conveyed on a troughed conveyor belt, a great deal of dust is created which can be both a health hazard and a fire hazard. In order to reduce this dust, systems have been developed for spraying water onto moving conveyor belts for keeping them and materials transported by them moist, thereby not allowing dust to develop. When such systems are employed, it is undesirable to spray too much water, because this creates unwanted water puddles and sludge which in turn must be cleaned up. For this reason, some such systems which have been suggested have involved monitoring the moisture level of the endless conveyor belts, and/or their contents, for controlling sprayers which spray water onto the belts for achieving desired moisture-content levels.

Prior art systems which have functioned as described above, have employed various types of sensors for sensing moisture levels of conveyor belts and their contents. However, some of these sensors have not properly functioned within the unfriendly environments of coal mines and coal transporting areas. That is, some such sensors have not been sturdy enough to withstand these unfriendly environments. Also, many such sensors have not been sufficiently accurate. Further, some such sensors have contacted the conveyor belts and in doing so have caused damage to the conveyor belts or, conversely, the conveyor belts have caused damage to the sensors. In this respect, U.S. Pat. No. 4,944,385 to Shelby discloses a particular endless belt moisture control apparatus whose sensors contact conveyor rollers which, in turn, contact a conveyor belt, so that damage to the conveyor belt and to the sensors is effectively avoided.

It is an object of this invention to provide a sensor device for a conveyor-belt moisture control sensor apparatus which is sturdy, accurate, relatively inexpensive and which does not easily damage a conveyor belt nor is easily damaged by the conveyor belt.

SUMMARY

According to principles of this invention, a sensor device for a conveyor-belt moisture control sensor apparatus comprises an electrically-insulative block having two adjacent electrodes attached thereto and being hingedly mounted on a conveyor-belt support frame for allowing the electrically-insulative block to rotate for bringing the two adjacent electrodes into contact with the conveyor belt. In one embodiment of the conveyor-belt moisture control sensor apparatus, the two adjacent electrodes are brought into contact with a top surface of a return portion of the conveyor belt, and in one embodiment two sensor wires mounted on the electrically-insulative block are attached to connection ends of the electrodes at points which are embedded in the electrically-insulative block.

BRIEF DESCRIPTION OF THE DRAWINGS

The invention is described and explained in more detail below using the embodiments shown in the drawings. The described and drawn features, in other embodiments of the invention, can be used individually or in preferred combinations. The foregoing and other objects, features and advantages of the invention will be apparent from the following more particular description of a preferred embodiment of the invention, as illustrated in the accompanying drawings in which reference characters refer to the same parts throughout the different views. The drawings are not necessarily to scale, emphasis instead being placed upon illustrating principles of the invention in a clear manner.

DESCRIPTION OF A PREFERRED EMBODIMENT

Figure 1:
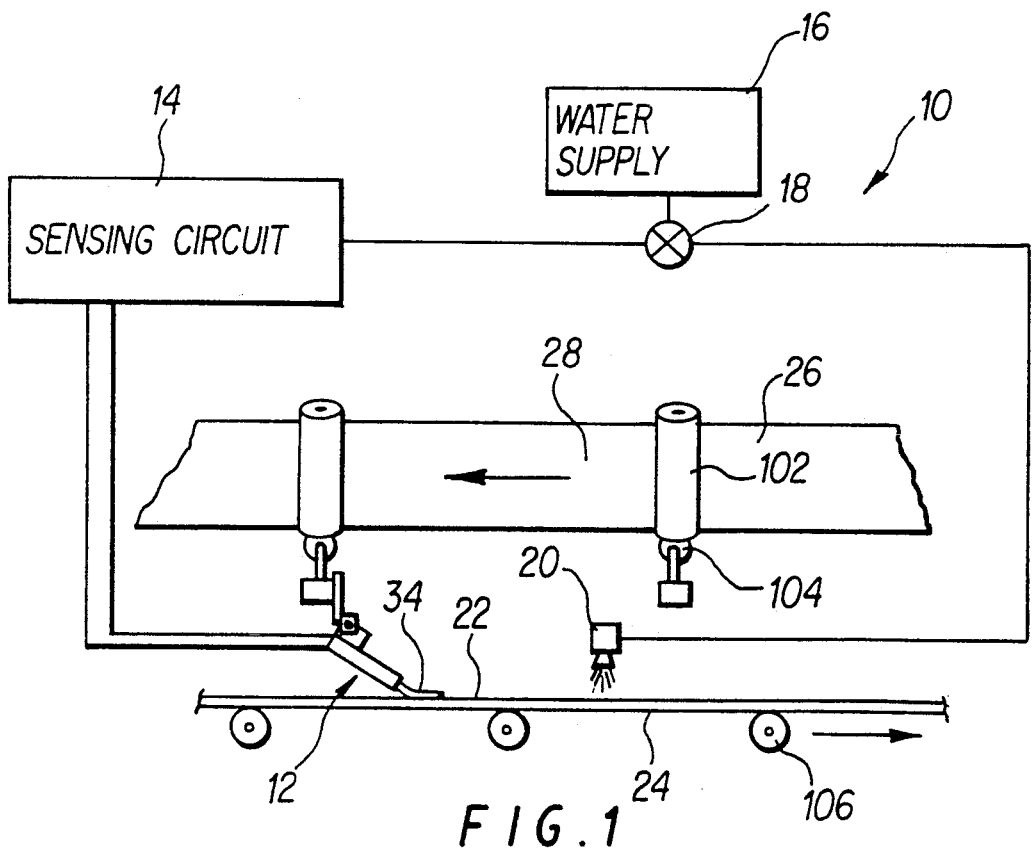
FIG. 1 is a schematic, simplified side view of a moisture control sensor apparatus of this invention.

A moisture control sensor apparatus 10 (FIG. 1) of this invention comprises a sensor device 12, a sensing circuit 14, a water supply 16, a valve 18, and a spray bar 20. Looking at FIG. 1, the sensor device 12 contacts a top surface 22 of a return portion 24 of an endless conveyor belt 26 and provides electronic sensing signals to the sensing circuit 14 which determines from these signals the moisture content of the endless conveyor belt 26 and, if it is not sufficiently moist, opens the valve 18 to thereby spray water from the water supply 16, via the spray bar 20, onto the return portion 24 of the conveyor belt 26. In this regard, in practice, such systems can also be used for spraying water on a top belt 28 of the endless conveyor belt 26, and/or on materials transported by the top belt 28 as well as on the return portion 24. It is significant that the sensor device 12 takes its reading from the top surface of the return portion inasmuch as prior-art moisture control systems normally took readings from the top belt 28 which contained aggregate, such as coal, to be transported.

Figure 2:
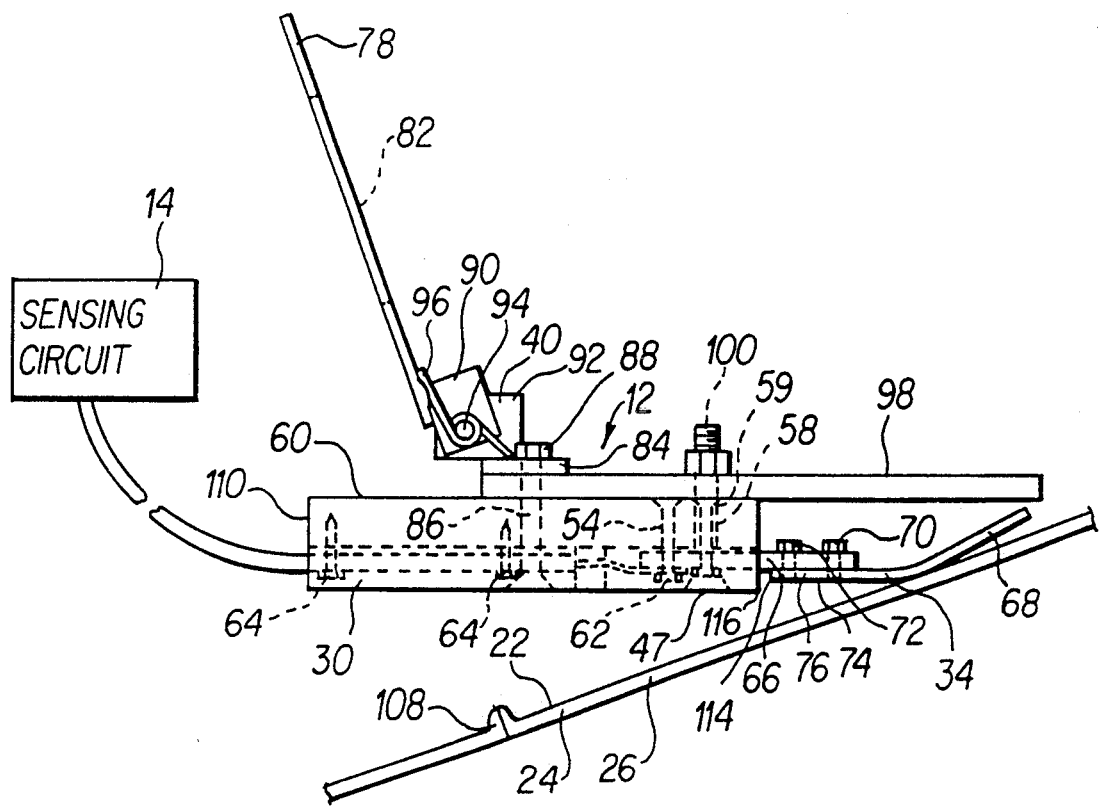
FIG. 2 is an enlarged, more detailed, side elevational view of a sensor device of the moisture control sensor apparatus of FIG. 1 with a segmented view of a conveyor belt being shown thereon and a sensing circuit being shown thereon in block-diagram form.
Figure 3:
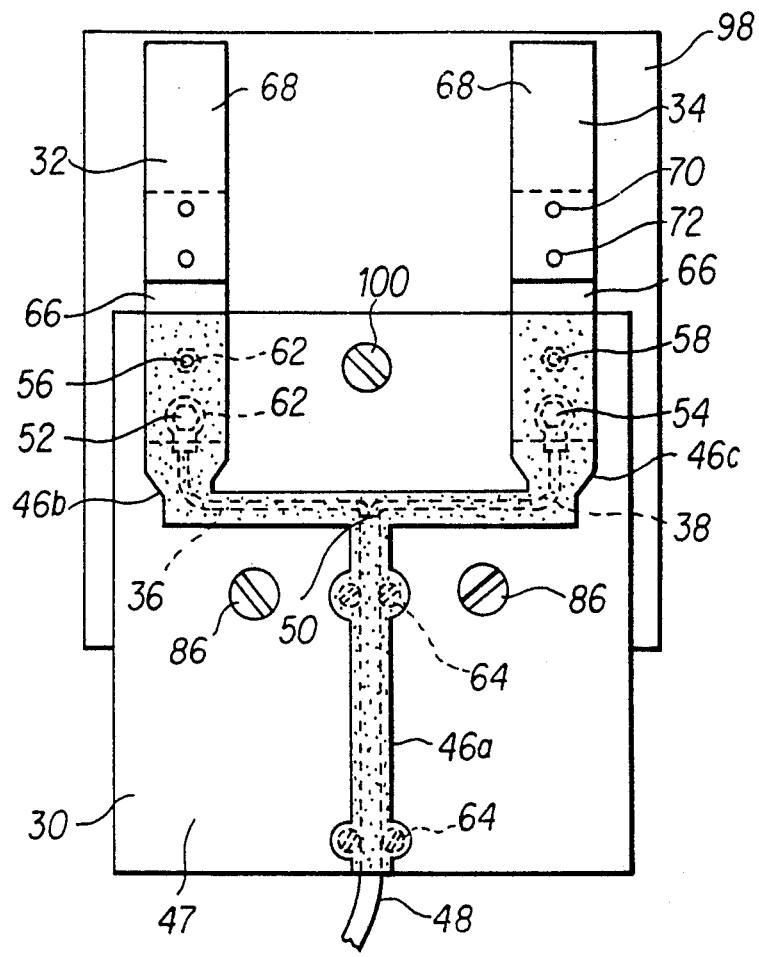
FIG. 3 is a bottom plan view of the sensor device of FIG. 2.
Figure 4:
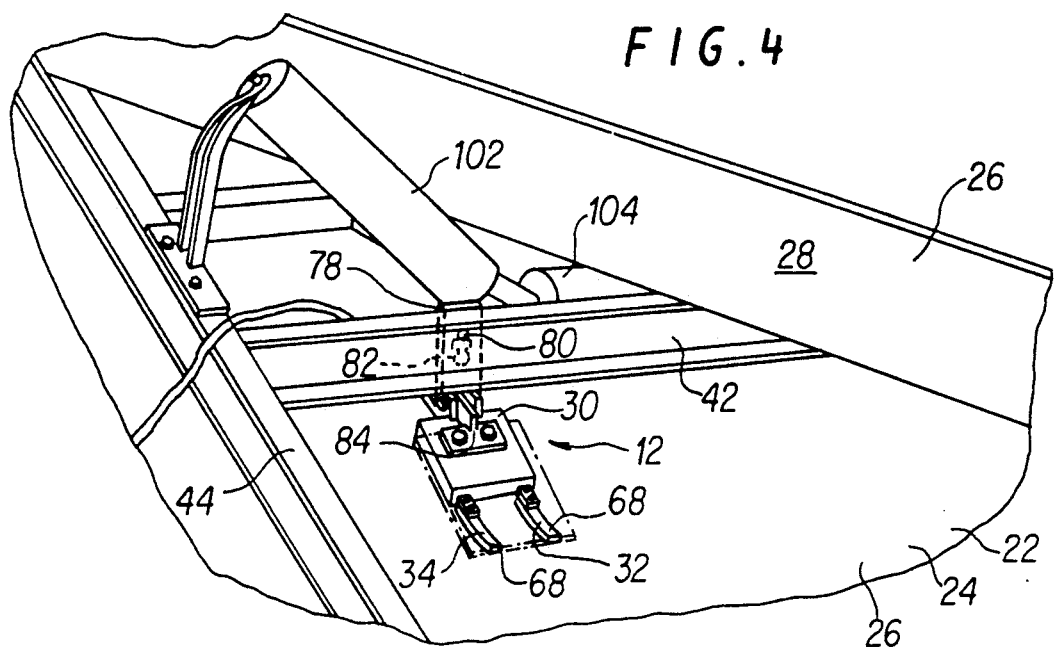
FIG. 4 is a segmented perspective view of an endless conveyor belt, a conveyor-belt support frame, conveyor idler rollers and a sensor device of this invention mounted on the conveyor-belt support frame.

Looking now at the sensor device 12 in more detail in FIGS. 2, 3, and 4, this device comprises an encapsulating electrically-insulative block 30 which is constructed of a single piece of UHMW plastic with spaced, adjacent electrodes 32 and 34 and wires 36 and 38 mounted thereon and extending therefrom. Fasteners for mounting and interconnecting the electrodes and wires are also part of the sensor device 12 as is a hinge mechanism 40 for rotatably mounting the electrically-insulative block 30 to a cross member 42 of a conveyor-belt support frame 44 (FIG. 4).

As mentioned above, the electrically-insulative block 30 is a single piece of insulative plastic and in one embodiment thereof a Y-shaped groove 46 is cut in a bottom surface 47 thereof to a depth of about one half the thickness of the electrically-insulative block 30. In a preferred embodiment, the electrically-insulative block 30 is approximately one inch thick with a length of approximately five inches and a width of approximately four and five eighth inches. In any event, a wire bundle 48, containing the wires 36 and 38 with a common insulation thereon, is mounted in a common portion 46a of the Y-shaped groove. An end 50 of the common insulation of the wire bundle 48 is approximately at the fork of the Y-shaped groove where the groove splits into two prongs 46b and 46c, with the two wires 36 and 38 then separating and extending into the respective prongs of the Y to be respectively attached to inner ends of the electrodes 32 and 34 by bolts 52 and 54 which also help to mount the electrodes 32 and 34 to the electrically-insulative block 30. In this regard, the electrodes 32 and 34 are mounted to the electrically-insulative block 30 by the bolts 52 and 54 as well as by bolts 56 and 58 which extend through the electrically-insulative block 30 to have heads 59 at a top surface 60 of the electrically-insulative block 30 and nuts 62 which are positioned in the Y-shaped groove 46. Heads of screws 64 which screw into the electrically-insulative block adjacent the wire bundle 48 hold the wire bundle in position. The Y-shaped groove 46 is filled with an insulative plastic, such as that which becomes an integral part of the block so that all of the elements depicted in dashed lines in FIG. 3 within the periphery of the electrically-insulative block 30 are encapsulated within the electrically-insulative block 30, including the filler insulative material, or resinous material, which fills the Y-shaped groove 46.

Examining the electrodes 32 and 34 (FIGS. 2, 3 and 4) in more detail, each of these elements is made up of an electrode holder 66 and an electrode feeler 68 which are interconnected by bolts 70 and 72. In this regard, holes in the electrode feelers 68 are female threaded to be engaged by male threads on the bolts 70 and 72 so that it is not necessary that these bolts extend a substantial distance beyond a bottom surface 74 of the electrode feelers 68 but rather the bolts 70 and 72 tighten in the threaded holes in the electrode feelers 68 to clamp the electrode holders 66 between heads of the bolts 70 and 72 and the electrode feelers 68.

Both the electrode holders 66 and the electrode feelers 68 are substantially rigid, being slightly less than ⅜ inch thick and having a width of approximately ¾ of an inch. In a preferred embodiment, the electrode holders 66 are constructed of brass, while the electrode feelers 68 are constructed of stainless steel. The electrode holders 66 are approximately 2 ¼ inches long while the electrode feelers 68 are approximately 3 inches long. Inner ends 76 of the electrode feelers 68, as can be seen in FIG. 2, overlap outer ends of the electrode holders 66 where they are screwed together by the bolts 70 and 72. Outer ends of the electrode feelers 68, which come into contact with the endless conveyor belt 26, bow, or bend, upwardly, away from the conveyor belt 26.

The hinge mechanism 40 comprises a frame hinge leg 78 for being attached to the cross member 42 of the conveyor support frame 44 by means of bolts 80 passing through a slot 82 in the frame hinge leg 78 and a sensor hinge leg 84 which is bolted to an inwardly-located portion of the electrically-insulative block 30 by means of bolts 86 passing through the electrically-insulative block 30 and the sensor hinge leg 84. Nuts 88 engage ends of the bolts 86. The frame hinge leg 78 is welded to frame hinge brackets 90 and the sensor hinge leg 84 is welded to a sensor hinge bracket 92. A hinge pivot pin 94 extends through these brackets for allowing relative rotation between the frame hinge leg 78 and the sensor hinge leg 84 to take place. A hinge bias spring 96 which extends about the hinge pivot pin 94 and impinges on the frame hinge leg 78 and the sensor hinge leg 84 biases these two numbers so that the electrodes 32 and 34 are urged toward the top surface 22 of the return portion 24 of the endless conveyor belt 26 when the frame hinge leg 78 is mounted on the cross member 42 as is depicted in FIG. 4.

A drip guard 98, constructed as a rectangular sheet of the same insulative material as is the electrically-insulative block 30, provides an embellishment of this invention by protecting the electrodes 32 and 34 from above. In this regard, the drip guard 98 is constructed of a single sheet of material, approximately ¼ inch thick and is bolted to the top surface 60 of the electrically-insulative block 30 by means of the bolts 85 and an additional bolt 100. In the embodiment depicted in FIG. 2, the sensor hinge leg 84 is actually mounted on top of the drip guard 98. The drip guard 98 extends outwardly from the electrically-insulative block 30 over external portions of the electrodes 32 and 34, that is, external portions of the electrode holders 66 and the electrode feelers 68.

Describing next operation of the moisture control sensor apparatus of this invention, the frame hinge leg 78 of the hinge mechanism 40 is mounted on the cross member 42 of the conveyor support frame 44. In this regard, the conveyor support frame 44 is primarily for supporting angled troughing idler rollers 102, horizontal troughing idler rollers 104 and return idler rollers 106. It should be understood that such conveyor support frames have many different configurations and that the hinge mechanism 40 can be adapted to fit the various configurations.

Once the sensor device 12 is mounted, it rotates about the hinge Pivot Pin 94, both because of gravity and because of the hinge bias spring 96, so that the electrode feelers 68 come into contact with the top surface 22 of the return portion 24 of the endless conveyor belt 26. The sensing circuit 14 applies a potential to the electrode feelers 68 via the wires 36 and 38 and in this manner measures a resistance between the electrode feelers 68. It will be understood by those of ordinary skill in the art that the resistance between the feelers 68 provides an indication of a moisture level on the endless conveyor belt 26. When the sensing circuit 14 determines that the moisture level has fallen below a preset threshold, it activates the valve 18 to furnish water from the water supply 16 to the sprayer bar 20, to moisten the top surface 22 of the return portion 24 of the endless conveyor belt 26. It should be noted that this device primarily controls water sprays on the bottom belt, or return portion, rather than on the conveyed material.

While the invention has been particularly shown and described with reference to a preferred embodiment, it will be understood by those of ordinary skill in the art that various changes in form and detail may be made therein without departing from the spirit and scope of the invention.

For example, although the invention is shown with only one sprayer, it should be understood that there could be other sprayers at other locations. There could be sprayers, for example, above the trough top belt 28 of the endless conveyor belt 26.

Also, the electrically-insulative block 30 as well as the drip guard 98 can be made using other non-conductive plastics, such as PVC, PTFE and Phenolic.

Further, it would be possible to replace the various nuts, bolts, and washers with molded elements which are molded as a part of the electrically-insulative block 30. Similarly, it would be possible to mold the drip guard 98 as one piece with the electrically-insulative block 30. If the various fasteners are molded with the electrically-insulative block 30, it is possible to reduce machining and hardware costs.

In one embodiment, the sensing circuit 14 also includes a LED indicator to indicate if water is spraying.

The electrode holders 66 could be constructed of conductive materials other than brass, such as copper or stainless steel.

The stainless steel electrode feelers 68 which are described above are of a 300-series chromium-nickel grade stainless steel. Other grades of stainless steel could be used such as a 400-series chromium type. The electrodes can also be made using a RQC-series (rolled, quenched carbon) which is a high-carbon steel.

It is beneficial that the electrode feelers 68 of the sensor device 12 contact the top surface 22 of the return portion 24 of the endless conveyor belt 26, because by doing so it operates on a clean portion of the endless conveyor belt.

Also, it is beneficial that the sensor device 12 comprises an electrically-insulative block 30 and a hinge mechanism for hingedly mounting the electrically-insulative block to the conveyor-belt support frame for allowing the electrically-insulative block to rotate. Not only is this structure sturdy, but the pair of electrode feelers thereof can automatically adjust to different positions and configurations of the return portion of the endless conveyor belt. That is, for example, with reference to FIG. 2, if the return portion 24 has an enlarged splice 108 therein, the electrically-insulative block 30 rotates to allow the electrode feelers to ride above the splice 108. Similarly, if the return portion 24 of the endless conveyor belt rises and falls, the electrode feelers 68 can also rise and fall due to operation of the hinge mechanism 40. Similarly, it is beneficial that the hinge mechanism 40 is not attached to the electrically-insulative block 30 at an end thereof, but rather to an inwardly-located portion thereof, located more towards a middle, or intermediate portion, of the block. By thusly mounting the hinge mechanism 40 to the block, it is possible to preset gravity-applied pressure of the electrode feelers 68 on the top surface 22. As can be seen in FIG. 2, the hinge pivot pin 94 is spaced inwardly from a rear end 110 of the electrically-insulative block 30 so as to reduce pressure applied by the electrode feelers 68 to the endless conveyor belt due to gravity and thereby cause less damage to the endless conveyor belt 22.

In some cases, it has been shown to be beneficial to include the hinge bias spring for biasing rotation of the electrically-insulative block toward bringing the electrodes into contact with the conveyor belt. Inclusion of the spring dampens pendulum motions of the electrically-insulative block 30 and thereby eliminates unduly long periods during which the electrodes are not in contact with the endless conveyor belt. Although the spring provides some biasing, most biasing is usually provided by gravity.

It is beneficial that points of attachment of the sensor wires 36 and 38 to the electrode holders 66 are encapsulated in the single-piece block, because in this manner the electrical connections are physically protected from unfriendly environments. Similarly, it is beneficial that the two sensor wires enter the encapsulated insulative block as a bundle and then are separated in an encapsulated area to attach to connector ends of the electrode holders 66.

It is further beneficial that the electrodes 32 and 34 are each formed of an embedded electrode holder member and an external, selectively-attachable electrode feeler. In this manner, the feeler can be serviced and replaced, if it becomes worn.

Similarly, it is beneficial that the electrode feelers 68 are attached to the electrode holders 66 by means of bolts 72 which pass through the electrode holders and engage threads in the electrode feelers, because in this manner these bolts do not need to extend outside of the electrode feelers, thereby causing projections which could snag on the endless conveyor belt 26. In the same manner, it is extremely helpful that bottom surfaces 74 of the electrode feelers 68 are above the plane of the bottom surface 47 of the electrically-insulative block 30 and that rear ends 114 of the electrode feelers 68 are close to a front end 116 of the electrically-insulative block 30, because in this manner it is assured that the rear ends 114 of the electrode feelers 68 do not contact portions of the endless conveyor belt 26, but rather projections from the endless conveyor belt 26, such as the splice 108 shown in FIG. 2, would first contact the bottom surface 47 of the electrically-insulative block 30 causing the block to rotate away from the conveyor belt 26.

The drip guard 98 is extremely beneficial in that it protects the electrodes 32 and 34 from water, and materials (such as "gobbing off") falling from above. That is, if wet materials are allowed to fall between the electrodes from above, this might provide false readings.

An unusual aspect of this invention is that the top surface 22 of the return portion 24 of the endless conveyor belt 26 is sensed to determine its moisture. Tests have shown that this method of monitoring the moisture content is sufficiently accurate and provides benefits which outweigh those of taking moisture measurements at the top belt 28 or at other locations thereon.

The sensor device of this invention causes very little, if any, damage to the endless conveyor. The embodiments of the invention in which an exclusive property or privilege are claimed are defined as follows:

I claim:

1. A moisture control sensor apparatus of a type including a sensing circuit coupled to a sensor device for sensing the relative moisture of a conveyor belt mounted on a conveyor-belt support frame, said sensor device comprising:

a single piece electrically-insulative block;

two adjacent electrodes extending from said electrically-insulative block, a connection end of each of said electrodes being mounted on said block;

at least two sensor wires mounted on said block, each of said sensor wires being attached to one of said connection ends of said electrodes and to a sensing circuit;

a hinge means attached to said electrically-insulative block and having a pivot mechanism located immediately adjacent said electrically insulative block for pivotally mounting said electrically-insulative block to said conveyor-belt support frame for allowing said electrically-insulative block to rotate at said pivot mechanism to thereby move said two adjacent electrodes relative to said conveyor-belt support frame for bringing said two adjacent electrodes into contact with said conveyor belt.

2. A moisture control sensor apparatus as in claim 1 wherein points of attachment of sensor wires to said attachment ends of said electrodes are encapsulated in said electrically-insulative block.

3. A moisture control sensor apparatus as in claim 2 wherein said at least two sensor wires enter said encapsulated insulative block as a bundle and separate therein to attach to said attachment ends.

4. A moisture control sensor apparatus as in claim 2 wherein said hinge means comprises a frame hinge leg and a sensor hinge leg connected by a pivotal mechanism defining a pivot axis, said frame hinge leg being attachable to said conveyor belt support frame and said sensor hinge leg being attachable to said electrically-insulative block.

5. A moisture control sensor apparatus as in claim 1 wherein each of said electrodes is comprised of an electrode holder and an electrode feeler selectively attachable to said electrode holder external of said electrically-insulative block.

6. A moisture control sensor apparatus as in claim 5 wherein said electrode holder and said electrode feeler are flat members which overlap at their attachment and which are attached to one another by screws which extend through the electrode holder and threadably engage the electrode feeler without substantially extending from a lower surface of the electrode feeler.

7. A moisture control sensor apparatus as in claim 6 wherein an end of said electrode feeler adjacent said block is substantially close to said block and a lower surface of the feeler is positioned above a lower surface of the electrically-insulative block.

8. A moisture control sensor apparatus for sensing the relative moisture of a conveyor belt mounted on a conveyor-belt support frame, said moisture control sensor apparatus including a sensor device comprising:
an electrically-insulative block;
two adjacent electrodes extending from said electrically-insulative block, a connection end of each of said electrodes being mounted on said block;
at least two sensor wires mounted on said block, each of said sensor wires being attached to one of said attachment ends of said electrodes;
a hinge means for hingedly mounting said electrically-insulative block to said conveyorbelt support frame for allowing said electrically-insulative block to rotate relative to said conveyor-belt support frame for bringing said two adjacent electrodes into contact with said conveyor belt wherein is further included a drip guard which extends from said block outwardly above said electrodes to protect said electrodes from materials falling toward said electrodes from above.

9. A moisture control sensor apparatus as in claim 8 wherein said drip guard is integral with said block.

10. A moisture control sensor apparatus as in claim 8 wherein each of said electrodes is comprised of an electrode holder and an electrode feeler selectively attachable to said electrode holder external of said electrically-insulative block.

11. A moisture control sensor apparatus as in claim 10 wherein said electrode holder and said electrode feeler are flat members which overlap at their attachment and which are attached to one another by screws which extend through the electrode holder and threadably engage the electrode feeler without substantially extending from a lower surface of the electrode feeler.

12. A moisture control sensor apparatus as in claim 11 wherein an end of said electrode feeler adjacent said block is substantially close to said block and a lower surface of the feeler is positioned above a lower surface of the electrically-insulative block.

13. A moisture control sensor apparatus as in claim 1 wherein said sensor device includes a spring biasing means for biasing rotation of said electrically-insulative block toward bringing said two adjacent electrodes into contact with a conveyor belt.

14. A moisture control sensor apparatus as in claim 1 wherein a sensing circuit attached to said two wires is for sensing when the resistance between the adjacent electrodes is at a predetermined threshold thereby indi7 cating a moisture on the conveyor belt of a predetermined level.

15. A moisture control sensor apparatus as in claim 1 wherein pivotal mechanism is spaced from and intermediate to front and rear edges of said electrically-insulative block.

16. A method of controlling moisture of material conveyed on an endless conveyor belt comprising the steps of:
mounting a moisture sensor or a support for pivotal movement above said conveyor belt;
sensing the moisture on an inner surface of a return portion of the endless conveyor belt with said sensor; and
in response to the moisture content of the inner surface of the return portion of the endless conveyor belt reaching a threshold of dryness, spraying a liquid on the endless conveyor belt.

17. A method as in claim 16 wherein the step of sensing the moisture on the inner surface of the return portion of the endless conveyor belt includes the substeps of contacting the inner surface with two electrodes and measuring the resistance between the two electrodes.

18. A method as in claim 17 wherein the substep of contacting the inner surface with the two electrodes includes the further steps of mounting the two electrodes on an electrically-insulative block, pivotally mounting the electrically-insulative block on a frame supporting the endless conveyor, and biasing the electrically-insulative block to pivot in a direction for bringing the two electrodes into contact with the inner surface.

* * * * *